United States Patent
Andre et al.

(10) Patent No.: US 7,182,938 B2
(45) Date of Patent: Feb. 27, 2007

(54) COSMETIC FORMULATIONS COMPRISING ZNO NANOPARTICLES

(75) Inventors: Valerie Andre, Ludwigshafen (DE); Richard W. Brotzman, Jr., Naperville, IL (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/074,760

(22) Filed: Mar. 9, 2005

(65) Prior Publication Data

US 2005/0255057 A1 Nov. 17, 2005

Related U.S. Application Data

(60) Provisional application No. 60/592,133, filed on Jul. 30, 2004, provisional application No. 60/559,857, filed on Apr. 6, 2004.

(51) Int. Cl.
*A61Q 17/04* (2006.01)
*A61Q 17/00* (2006.01)
*A61Q 19/00* (2006.01)
*A61K 8/00* (2006.01)
*A61K 8/04* (2006.01)

(52) U.S. Cl. .......... 424/59; 424/60; 424/400; 424/401

(58) Field of Classification Search .......... 424/59, 424/60, 400, 401
See application file for complete search history.

(56) References Cited

U.S. PATENT DOCUMENTS 5,993,967 A * 11/1999 Brotzman et al. .......... 428/407
6,033,781 A    3/2000 Brotzman, Jr. et al.
2005/0222325 A1 10/2005 Brotzman, Jr.

* cited by examiner

*Primary Examiner*—Shelley A. Dodson
(74) *Attorney, Agent, or Firm*—Oblon, Spivak, McClelland, Maier & Neustadt, P.C.

(57) ABSTRACT

The present invention relates to the formation of surface treated zinc oxide and titania particles, and in particular zinc oxide and titania nanoparticles, with a siloxane star-graft copolymer coating, comprising a looped and/or linear polymeric structure on a star-graft copolymer coating, on a particle surface to control the interfacial surface interactions between the particle and the oil phase of the cosmetic skin formulation.

13 Claims, No Drawings

COSMETIC FORMULATIONS COMPRISING ZNO NANOPARTICLES

CROSS-REFERENCE TO RELATED PATENTS

Particulate surfaces, and in particular nanoparticle surfaces, may be surface treated by star-graft copolymers to form uniform coatings according to the methods disclosed in U.S. Pat. Nos. 5,993,967 and 6,033,781, which are incorporated herein by reference.

FIELD OF THE INVENTION

Modern skin care formulations must meet high standards of efficacy, skin compatibility and aesthetic appeal. It is commonly accepted that the performance of a cosmetic product is related to the entire formulation. Thus, an optimal galenic formulation that incorporated active ingredients is a necessary prerequisite to succeed in the market. The objective of topical formulations may be classified in two major areas: to modulate or assist the barrier function of the skin and to act as a delivery system for active ingredients. This patent focuses on the development of galenically interesting formulation concepts used in contemporary skin care products which combine, in particular, charged organic moieties, such as acrylate-based polymers, $\alpha$- and $\beta$-hydroxy acids, etc., and inorganic zinc oxide and titania.

The present invention relates in particular to problems encountered when particulate zinc oxide, and in particular nanoparticulate zinc oxide, is formulated with charged organic moieties, such as acrylate-based polymers, $\alpha$- and $\beta$-hydroxy acids, etc. Contemporary skin care formulations are dispersions. The charged organic moieties will reside in the aqueous phase of the dispersion and the inorganic ingredients, zinc oxide and titania, reside in the oil phase of the dispersion. In formulation the acrylate-based polymers, once neutralized with a cosmetically acceptable base such as triethanol amine or sodium hydroxide, extend to thicken the formulation by increasing the viscosity of the aqueous phase. Other charged organic moieties, such as $\alpha$- and $\beta$-hydroxy acids, may have other functions such as enhancing epithelial cell regeneration. However zinc ions from the particulate zinc oxide migrate from the oil phase to the aqueous phase and adversely interact with the charged organic moieties to either cause collapse of the acrylate-based polymers or the formation of organic salts with concomitant dissolution of the particulate inorganic.

Specifically excluded from the present invention are surface treatments for all inorganic, semi-metallic, and/or metallic oxide particles for all applications except (a) the product(s) per se, defined as surface treated ZnO and/or $TiO_2$ (titania), and (b) the use of the product(s) per se in personal care formulations. Personal care formulations are defined as cosmetic or dermatological preparations for skin care, hair care, foot care, sun care, oral care, baby care, toiletries, color cosmetics, personal cleaning, and topical human sunscreens.

INVENTION

The present invention relates to the formation of surface treated zinc oxide and titania particles, and in particular zinc oxide and titania nanoparticles, with a siloxane star-graft copolymer coating, comprising a looped and/or linear polymeric structure on a star-graft copolymer coating, on a particle surface to control the interfacial surface interactions between the particle and the oil phase of the cosmetic skin formulation. The siloxane star-graft copolymer, that may or may not contain topological loops, is formed in the "particle surface proximity" by a heterogeneous polymerization reaction. The resulting surface treatment will passivate the zinc oxide surface to prevent ion leakage and render the surface treated zinc oxide compatible with charged organic moieties, such as acrylate-based polymers and $\alpha$- and $\beta$-hydroxy acids, etc. In addition the surface treatment on zinc oxide and titania can be tailored to render the surface treated particle thermodynamically compatible with different oil phase components of a cosmetic skin formulation.

BACKGROUND OF THE INVENTION

The surface treatment of inorganic particles has been addressed over the years by many different techniques and chemical efforts. Some of the techniques are the application of coatings to the surface of particles, using coupling agents on the surface of the particles, physically modifying the surface of the particles, chemically modifying the innate composition on the surface of the particles, and/or modifying the formulation to accommodate the particle—this latter is one of the least desirable methods of controlling particulate behavior in formulation as it limits formulation composition and ingredients and may alter essential formulation and product properties.

The surfaces of zinc oxide and titania have been conventionally coated by adsorption, ion exchange, and covalent bonding. Adsorption and ion exchange require the surface to have the appropriate chemical characteristics. Reactions that enable covalent bonding to particle surfaces generally involve reactions with a surface-bound hydroxyl group. These coatings are thin surface treatments which afford a degree of formulation and product compatibility and for the best available technology no particulate aggregation, but can not prevent ion migration from reactive particles or affect ultimate control of interfacial material properties.

DESCRIPTION OF INVENTION

The shortcomings of the existing art are overcome and additional advantages are provided through the provision of a surface treated zinc oxide and/or titania nanoparticle having a coating comprised of a star-graft siloxane copolymer to which are polymerized looped and/or linear polymer chains. Particulate surfaces, and in particular nanoparticulate surfaces, may be surface treated by siloxane star-graft copolymers to form uniform coatings according to the methods disclosed in U.S. Pat. Nos. 5,993,967 and 6,033,781 which are incorporated herein by reference. These uniform particulate surface treatments enable compatibility without particulate aggregation but they are subject to the limitations enumerated above. These star-graft copolymers may be formulated to have pendant groups that are reactive. It is to these reactive pendant groups that difunctional monomers are graft copolymerized to form looped and/or linear chains.

The star-graft copolymers may be applied to zinc oxide and/or titania particles, and in particular nanoparticles. The star-graft copolymer coatings are formed by reacting specific monomers to form a siloxane-based polymer. The surface treatment encapsulates the nanoparticulate zinc oxide and/or titania. In general, a plurality of nanoparticle zinc oxide and/or titania is surface treated with the star-graft copolymer and the surface treatment encapsulates at least a portion of the particles discretely, preferably all of the particles discretely. The star-graft copolymer, disclosed in U.S. Pat. No. 5,993,967 and U.S. Pat. No. 6,033,781, comprises:

Si (w, x, y, z)

where w, x, y, and z are the mole percent tetrafunctional, trifunctional, difunctional, and monofunctional monomeric units, respectively and wherein w, x, y, and z ranges of about 45–75, 5–25, 5–45, and 5–10, respectively.

As disclosed in U.S. Pat. Nos. 5,993,967 and 6,033,781, a star-graft copolymer, capable of coating and encapsulating nanoparticles, required a relatively large percentage of tetrafunctional monomers to yield a high degree of branching. In addition, the trifunctional monomers directed coating conformation, difunctional monomers were the linear polymer segments, and monofunctional monomers controlled the overall size Because difunctional monomers are polymerized to this star-graft polymer to form looped and/or linear polymer chains that extend from the particle surface into the solvating fluid or matrix structure, one skilled in the art would expect that a decrease the monofunctional monomer to enable the star-graft polymer surface treatment to retain functionality, and increase the difunctional monomers to form additional linear polymer segments would be yield the desired surface treatment. However to our surprise, not only was it necessary to decrease the monofunctional monomers to retain functionality on the star-graft polymer and to increase the difunctional monomers to form additional linear chains, but the present invention further requires the star-graft copolymer to have a significantly lower degree of branching, with respect to surface treatments taught in U.S. Pat. Nos. 5,993,967 and 6,033,781—this is an unexpected and surprising result.

It is these looped and/or linear polymer chains that enable surface treatments, what would otherwise be thin coatings, to extend into the application medium and control the interfacial properties of the zinc oxide and/or titania particle.

The present invention relates to a surface treated particle comprising a plurality of zinc oxide and/or titania particles and a star-graft copolymer with looped and/or linear polymeric structure on a star-graft copolymer encapsulating at least a portion of said particles, said surface treatment comprising:

Si (x, y)

where x and y are the mole percent trifunctional and difunctional monomeric units, respectively.

In the preferred surface treated particle:

x is selected from the group of trifunctional monomers that have cosmetically acceptable non-reactive ligands comprising of methyltrimethoxysilane, n-propyltrimethoxysilane, isobutyltrimethoxysilane, n-hexyltrimethoxysilane, n-octyltrimethoxysilane, n-octadecyltrimethoxysilane, phenyltrimethoxysilane, and the triethoxy-containing counterparts of these monomers; and y is selected from the group of difunctional monomers that have cosmetically acceptable non-reactive ligands comprising of dicyclohexyldimethoxysilane, diethyldiethoxysilane, dimethyldichlorosilane, dimethyldiethoxysilane, dimethyldimethoxysilane, diphenyldiethoxysilane, diphenyldimethoxysilane, di-n-hexyldichlorosilane, n-hexylmethyldichlorosilane, methyldodecyldiethoxysilane, n-octylmethyldimethoxysilane, and the diethoxy-containing counterparts of these monomers.

In the most preferred surface treated particle:

x is selected from the group of n-octyltrimethoxysilane, n-octyltriethoxysilane, phenyltrimethoxysilane and phenyltriethoxysilane; and y is selected from the group of diphenyldiethoxysilane and diphenyldimethoxysilane.

The values of x and y in the above silicon-based polymers have ranged from 1–50 and 50–99, respectively. Preferably the values of x and y in the above silicon-based polymers have ranged from 1–40 and 60–99, respectively. Most preferably the values of x and y in the above silicon-based polymers have ranged from 10–30 and 70–90, respectively.

The surface treatment is applied to zinc oxide and/or titania particles, and in particular nanoparticles. The nanoparticle mean particle size range is from about 1 nm to about 900 nm. The preferred nanoparticle mean particle size range is from about 2 nm to about 500 nm. The most preferred nanoparticle mean particle size range is from about 5 nm to about 100 nm.

As an alternative to processing methods disclosed in U.S. Pat. Nos. 5,993,967 and 6,033,781, the preferred method of preparing the surface treated zinc oxide and/or titania comprises mixing the particulate comprising substantially spherical nanocrystalline particles with surface treatment precursors. The siloxane star-graft copolymer, that contains loops and/or linear polymer chains, is formed in the "particle surface proximity" by a heterogeneous polymerization reaction. The mixture is carried out at a temperature, in an environment, and for a time that is effective for the star-graft copolymer to coat the nanocrystalline particle and the difunctional precursors to polymerize to form the looped and/or linear chain surface treatment morphology. Volatile by-products may be driven off as the surface treated powder is heated. The nanoparticles and the coating precursor are added in quantities effective to enable chemically passive surface treatments that prevent ion leakage and render the surface treated zinc oxide compatible with charged organic moieties, such as acrylate-based polymers, $\alpha$- and $\beta$-hydroxy acids. The amount of coating precursor used is directly related to the particle surface area or the particle size.

DETAILED DESCRIPTION OF THE INVENTION

In accordance with the principles of the present invention, a surface treatment of zinc oxide and/or titania particles, and in particular the surface treated nanoparticles, with looped and/or linear polymeric structure on a star-graft polymer coating on a particle surface and method for making the same are provided. To passivate the zinc oxide surface to prevent ion leakage and render the surface treated zinc oxide compatible with charged organic moieties, such as acrylate-based polymers, $\alpha$- and $\beta$-hydroxy acids, etc., the surface treatment contains predominantly phenyl chemistry. In addition the surface treatment on zinc oxide and titania can be tailored to render the surface treated particle thermodynamically compatible with different oil phase components of a cosmetic skin formulation, by judicious selection of non-phenyl containing precursors.

The surface treatment is applied to zinc oxide and/or titania particles, and in particular nanoparticles. The nanoparticle mean particle size range is from about 1 nm to about 900 nm. The preferred nanoparticle mean particle size range is from about 2 nm to about 500 nm. The most preferred nanoparticle mean particle size range is from about 5 nm to about 100 nm.

The values of x and y in the above silicon-based polymers have ranged from 1–50 and 50–99, respectively. Preferably the values of x and y in the above silicon-based polymers have ranged from 1–40 and 60–99, respectively. Most preferably the values of x and y in the above silicon-based polymers have ranged from 10–30 and 70–90, respectively.

Various combinations are employed to control the branching of the siloxane backbone, the degree of looped and/or linear chains, and its chemical nature, that is, the degree of thermodynamic compatibility with specific oil phase components of a cosmetic skin formulation. Additionally the chemical nature of the difunctional monomers are selected to transform what would otherwise be thin coatings, into loops and/or linear chains that extend into the oil phase components of a cosmetic skin formulation medium.

The invention also relates to a method of protecting human skin or human hair from ultraviolet radiation comprising treating said skin or hair with an effective protecting concentration of a surface treated particle comprising a plurality of zinc oxide and/or titania particles and a star-graft copolymer with looped and/or linear polymeric structure on a star-graft copolymer encapsulating at least a portion of said particles, said surface treatment comprising:

$$Si\ (x, y)$$

where x and y are mole percent trifunctional and difunctional monomeric units, respectively and wherein x and y are about 1–50 and 50–99, respectively, wherein:

x is selected from the group of trifunctional monomers that have cosmetically acceptable non-reactive ligands comprising of methyltrimethoxysilane, n-propyltrimethoxysilane, isobutyltrimethoxysilane, n-hexyltrimethoxysilane, n-octyltrimethoxysilane, n-octadecyltrimethoxysilane, phenyltrimethoxysilane, and the triethoxy-containing counterparts of these monomers;

y is selected from the group of difunctional monomers that have cosmetically acceptable non-reactive ligands comprising of dicyclohexyldimethoxysilane, diethyldiethoxysilane, dimethyldichlorosilane, dimethyldiethoxysilane, dimethyldimethoxysilane, diphenyldiethoxysilane, diphenyldimethoxysilane, di-n-hexyldichlorosilane, n-hexylmethyldichlorosilane, methyldodecyldiethoxysilane, n-octylmethyldimethoxysilane, and the diethoxy-containing counterparts of these monomers, where the product(s) per se, defined as surface treated ZnO and/or TiO$_2$, are used in personal care formulations.

In a preferred variant of the method the surface treatment comprising:

$$Si\ (x, y)$$

wherein x and y are about 10–30 and 70–90, respectively, wherein:

x is selected from the group of n-octyltrimethoxysilane, n-octyltriethoxysilane, phenyltrimethoxysilane and phenyltriethoxysilane, and y is selected from the group of n-octyltrimethoxysilane, n-octyltriethoxysilane.

According to one variant of the method the said effective protecting concentration ranges between 0.1% and 25% by weight, preferably between 0.1% and 10%, particularly preferably between 1% and 7%, based on the total weight of the personal care formulation.

In a preferred variant of the method the said personal care formulation comprises surface treated zinc oxide and/or titanium dioxide particles alone or together with compounds which absorb in the UV region and are known for cosmetic and pharmaceutical preparations.

Accordingly, the present invention also relates to sunscreen-containing personal care formulations for protecting human skin or human hair from ultraviolet radiation, which comprises, in a cosmetically and pharmaceutically suitable carrier, an effective protecting concentration of a surface treated particle comprising a plurality of zinc oxide and/or titania particles and a star-graft copolymer with looped and/or linear polymeric structure on a star-graft copolymer encapsulating at least a portion of said particles, said coating polymer comprising:

$$Si\ (x,y)$$

where x and y are the mole percent trifunctional and difunctional monomeric units, respectively, and wherein x is about 1–50 and y is about 50–99, respectively, wherein:

x is selected from the group of trifunctional monomers that have cosmetically acceptable non-reactive ligands comprising of methyltrimethoxysilane, n-propyltrimethoxysilane, isobutyltrimethoxysilane, n-hexyltrimethoxysilane, n-octyltrimethoxysilane, n-octadecyltrimethoxysilane, phenyltrimethoxysilane, and the triethoxy-containing counterparts of these monomers;

y is selected from the group of difunctional monomers that have cosmetically acceptable non-reactive ligands comprising of dicyclohexyldimethoxysilane, diethyldiethoxysilane, dimethyldichlorosilane, dimethyldiethoxysilane, dimethyldimethoxysilane, diphenyldiethoxysilane, diphenyldimethoxysilane, di-n-hexyldichlorosilane, n-hexylmethyldichlorosilane, methyldodecyldiethoxysilane, n-octylmethyldimethoxysilane, and the diethoxy-containing counterparts of these monomers.

Particular preference is given to personal care formulations wherein the said surface treatment comprising:

$$Si\ (x, y)$$

wherein x and y are about 10–30 and 70–90, respectively, wherein:

x is selected from the group of n-octyltrimethoxysilane, n-octyltriethoxysilane, phenyltrimethoxysilane and phenyltriethoxysilane, and y is selected from the group of n-octyltrimethoxysilane, n-octyltriethoxysilane.

The cosmetic and dermatological preparations according to the invention can comprise cosmetic active ingredients, auxiliaries and/or additives, for example, coemulsifiers, fats and waxes, stabilizers, thickeners, biogenic active ingredients, film formers, fragrances, dyes, pearlizing agents, preservatives, pigments, electrolytes (e.g. magnesium sulfate) and pH regulators.

Suitable coemulsifiers are, preferably, known W/O and also O/W emulsifiers, such as, for example, polyglycerol esters, sorbitan esters or partially esterified glycerides. Typical examples of fats are glycerides; waxes which may be mentioned are inter alia beeswax, paraffin wax or microcrystalline waxes, optionally in combination with hydrophilic waxes. Stabilizers which may be used are metal salts of fatty acids, such as, for example, magnesium, aluminum and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, and also fatty alcohols, monoglycerides and fatty acids, polycrylates, polyvinyl alcohol and polyvinylpyrrolidone. The term biogenic active ingredients means, for example, plant extracts, protein hydrolyzates and vitamin complexes. Customary film formers are, for example, hydrocolloids, such as chitosan, microcrystalline chitosan or quaternary chitosan, polyvinylpyrrolidone, vinylpyrrolidone/vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlizing agents are glycol distearic esters, such as ethylene glycol distearate, but also fatty acids and fatty acid monoglycol esters. Dyes which may be used are the substances suitable and approved for cosmetic purposes, as listed, for example, in the publication "Kosmetische Färbemittel" [Cosmetic Colorants] from the Farbstoffkommission der Deutschen Forschungsgemeinschaft [Dyes Commission of the German Research Council], published by Verlag Chemie, Weinheim, 1984. These dyes are usually used in a concentration of from 0.001 to 0.1% by weight, based on the total mixture.

It is likewise advantageous to add customary antioxidants to the preparations for the purposes of the present invention. According to the invention, all antioxidants which are customary or suitable for cosmetic and dermatological applications may be used as favorable antioxidants.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, retinoids, such as, for example, retinol, retinal and/or retinoic acid and the respective esters, α-lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, 2-aminopropionic acid diacetic acid, flavonoids, polyphenols, catechins, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), and coniferyl benzoate of benzoin resin, rutinic acid and derivatives thereof, ferulic acid and derivatives thereof, butylhydroxytoluene, butylhydroxyanisole, nordihydroguaiacic acid, nordihyrdoguaiaretic acid, trihydroxybutyrophenone, uric acid and derivatives thereof, mannose and derivatives thereof, zinc and derivatives thereof, (e.g. ZnO, ZnSO.sub.4), selenium and derivatives thereof (e.g. selenomethionine), stilbene and derivatives thereof (e.g. silbene oxide, trans-stilbene oxide) and the derivatives (salts, esters, ethers, sugars, nucleotides, nucleosides, peptides and lipids) of said active ingredients which are suitable according to the invention.

The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and/or derivatives thereof are the antioxidant or antioxidants, it is advantageous to choose their respective concentrations from the range 0.001 to 10% by weight, based on the total weight of the formulation.

If vitamin A and/or derivatives thereof or carotenoids are the antioxidant or antioxidants, it is advantageous to choose the respective concentration thereof from the range 0.001 to 10% by weight, based on the total weight of the formulation.

If the cosmetic or dermatological preparation for the purposes of the present invention is a solution or emulsion or dispersion, the solvents used may be:

water or aqueous solutions; oils, such as triglycerides of capric acid or of caprylic acid, but preferably castor oil; fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids; alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monethyl ether and analogous products.

In particular, mixtures of the above mentioned solvents are used. In the case of alcoholic solvents, water may be a further constituent.

The oil phase of the emulsions, oleogels or hydrodispersions or lipodispersions for the purposes of the present invention is advantageously chosen from the group of esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms, from the group of esters of aromatic carboxylic acids and saturated and/or unsaturated, branched and/or unbranched alcohols with a chain length of from 3 to 30 carbon atoms. Such ester oils can then advantageously be chosen from the group consisting of isopropyl myristate, isopropyl palmitate, isopropyl stearate, isopropyl oleate, n-butyl stearate, diisopropyl adipate, n-hexyl laurate, n-decyl oleate, glyceryl stearate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of said esters, e.g. jojoba oil.

In addition, the oil phase can advantageously be chosen from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids with a chain length of from 8 to 24, in particular 12–18, carbon atoms. The fatty acid triglycerides can, for example, be chosen advantageously from the group of synthetic, semisynthetic and natural oils, e.g. olive oil, sunflower oil, soybean oil, peanut oil, rapeseed oil, almond oil, palm oil, coconut oil, palm kernel oil and the like.

Any mixtures of such oil and wax components are also to be used advantageously for the purposes of the present invention. It may in some instances also be advantageous to use waxes, for example cetyl palmitate, as the sole lipid component of the oil phase.

The oil phase is advantageously chosen from the group consisting of 2-ethylhexyl isostearate, isohexadecane, octyldodecanol, isotridecyl isononanoate, isoeicosane, 2-ethylhexyl cocoate, $C_{12}$–$C_{15}$-alkyl benzoate, caprylic/capric acid triglyceride, dicaprylyl ether.

Mixtures of $C_{12}$–$C_{15}$-alkyl benzoate and 2-ethylhexyl isostearate, mixtures of $C_{12}$–$C_{15}$-alkyl benzoate and isotridecyl isononanoate, and mixtures of $C_{12}$–$C_{15}$-alkyl benzoate, 2-ethylhexyl isostearate and isotridecyl isononanoate are particularly advantageous.

Of the hydrocarbons, paraffin oils, squalane and squalene are to be used advantageously for the purposes of the present invention.

Advantageous oil components are also, for example, butyloctyl salicylate (for example that available under the trade name Hallbrite BHB from CP Hall), hexadecyl benzoate and butyloctyl benzoate and mixtures thereof (Hallstar AB) and/or diethylhexyl naphthalate (Hallbrite TQ).

The oil phase can also advantageously have a content of cyclic or linear silicone oils, or consist entirely of such oils, although it is preferred to use an additional content of other oil phase components apart from the silicone oil or the silicone oils.

Advantageously, cyclomethicone (octamethylcyclotetrasiloxane) is used as silicone oil to be used according to the invention. However, other silicone oils can also be used advantageously for the purposes of the present invention, for example hexamethylcyclotrisiloxane, polydimethylsiloxane, poly(methylphenylsiloxane).

Mixtures of cyclomethicone and isotridecyl isononanoate, and of cyclomethicone and 2-ethylhexyl isostearate are also particularly advantageous.

Solid sticks comprise, for example, natural or synthetic waxes, fatty alcohols or fatty acid esters. Preference is given to using lip care sticks, and stick formulations for deodorizing the body.

Customary basic substances which are suitable for use as cosmetic sticks for the purposes of the present invention are liquid oils (e.g. paraffin oils, castor oil, isopropyl myristate), semisolid constituents (e.g. petroleum jelly, lanolin), solid constituents (e.g. beeswax, ceresin and microcrystalline waxes and ozocerite), and high-melting waxes (e.g. carnauba wax, candelilla wax).

Suitable propellants for cosmetic and/or dermatological preparations for the purposes of the present invention which can be sprayed from aerosol containers are the customary known readily volatile, liquefied propellants, for example hydrocarbons (propane, butane, isobutane), which can be used on their own or in a mixture with one another. Compressed air can also be used advantageously.

The person skilled in the art is of course aware that there are propellant gases which are nontoxic per se which would in principle be suitable for realizing the present invention in the form of aerosol preparations, but which nevertheless have to be avoided due to a harmful effect on the environment or other accompanying phenomena, in particular fluorocarbons and chlorofluorocarbons (CFCs).

Cosmetic preparations for the purposes of the present invention may also be in the form of gels which, besides an effective content of active ingredient according to the invention and solvents customarily used therefore, preferably water, also comprise organic thickeners, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickeners, e.g. aluminum silicates, such as, for example, bentonites, or a mixture of polyethylene glycol and polyethylene glycol stearate or distearate. The thickener is present in the gel, for example, in an amount between 0.1 and 30% by weight, preferably between 0.5 and 15% by weight. The cosmetic and pharmaceutical preparations comprising light protection agents are generally based on a carrier which comprises at least one oil phase. Preparations based solely on aqueous components are, however, also possible. Accordingly, suitable preparations are oils, oil-in-water and water-in-oil emulsions, creams and pastes, lip-protection stick compositions or grease-free gels.

Gels used according to the invention usually comprise alcohols of low carbon number, e.g. ethanol, isopropanol, 1,2-propanediol, glycerol and water or an abovementioned oil in the presence of a thickener, which in the case of oily-alcoholic gels is preferably silicon dioxide or an aluminum silicate, and in the case of aqueous-alcoholic or alcoholic gels is preferably a polyacrylate.

The total proportion of auxiliaries and additives can be 1 to 80% by weight, preferably 6 to 40% by weight, and the nonaqueous proportion ("active substance") can be 20 to 80% by weight, preferably 30 to 70% by weight, based on the compositions. The compositions can be prepared in a manner known per se, i.e. for example by hot, cold, hot-hot/cold or PIT emulsification. This is a purely mechanical process, and no chemical reaction takes place.

Such sunscreen preparations can accordingly be in liquid, paste or solid form, for example as water-in-oil creams, oil-in-water creams and lotions, aerosol foam creams, gels, oils, marking pencils, powders, sprays or alcohol-aqueous lotions.

According to the application technology requirements the surface treated particles (ZnO and/or $TiO_2$) can be added either to the oil or to the aqueous phase of the cosmetic preparation.

Finally, it is possible additionally to use further substances known per se which absorb in the UV region, provided they are stable in the overall system of the combination of UV filters to be used according to the invention.

The majority of light protection agents in the cosmetic and pharmaceutical preparations used to protect the human epidermis consists of compounds which absorb UV light in the UV-B region, i.e. in the range from 280 to 320 nm and UV-A region, i.e. in the range from 320 to 400 nm. For example, the proportion of the UV-A absorbers to be used according to the invention is 10 to 90% by weight, preferably 20 to 50% by weight, based on the total amount of UV-B and UV-A absorbing substances.

Suitable UV filter substances which are used in combination with the formulations to be used according to the invention are any UV-A and UV-B filter substances. Examples which may be mentioned are:

| No. | Substance | CAS No. (=acid) |
|---|---|---|
| 1 | 4-Aminobenzoic acid | 150-13-0 |
| 2 | 3-(4'-Trimethylammonium)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxy-benzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)-bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxy-benzophenone-5-sulfonic acid (sulisobenzone) and the sodium salt | 4065-45-6 |
| 13 | 3-(4'-Sulfobenzylidene)bornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-Trianiline(o-carbo-2'-ethylhexyl-1'-oxy)-1,3,5-triazine | 88122-99-0 |
| 18 | 3-Imidazol-4-ylacrylic acid and its ethyl ester | 104-98-3 |
| 19 | Ethyl 2-cyano-3,3-diphenylacrylate | 5232-99-5 |
| 20 | 2'-Ethylhexyl 2-cyano-3,3-diphenylacrylate | 6197-30-4 |
| 21 | Menthyl o-aminobenzoate or: 5-methyl-2-(1-methylethyl)-2-aminobenzoate | 134-09-8 |
| 22 | Glyceryl p-aminobenzoate or: 1-glyceryl 4-aminobenzoate | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxalic acid or: sodium 3,4-dimethoxyphenylglyoxalate | 4732-70-1 |
| 27 | 3-(4'Sulfobenzylidene)bornan-2-one and its salt | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |
| 30 | 2,2'-Methylenebis[6(2H-benzotriazol-2-yl)-4-(1,1,3,3-tetramethylbutyl)phenol] | 103597-45-1 |
| 31 | 2,2'-(1,4-Phenylene)-bis-1H-benzimidazole-4,6-disulfonic acid, Na salt | 180898-37-7 |
| 32 | 2,4-bis[4-(2-Ethylhexyloxy)-2-hydroxy]phenyl-6-(4-methoxyphenyl)-(1,3,5)-triazine | 187393-00-6 |
| 33 | 3-(4-Methylbenzylidene)camphor | 36861-47-9 |
| 34 | Polyethoxyethyl 4-bis(polyethoxy)paraaminobenzoate | 113010-52-9 |
| 35 | 2,4-Dihydroxybenzophenone | 131-56-6 |
| 36 | 2,2'-Dihydroxy-4,4'-dimethoxybenzophenone-5,5'-disodium sulfonate | 3121-60-6 |
| 37 | Benzoic acid, 2-[4-(diethylamino)-2-hydroxybenzoyl]-, hexylester | 302776-68-7 |
| 38 | 2-(2H-Benzotriazol-2-yl)-4-methyl-6-[2-methyl-3-[1,3,3,3-tetramethyl-1-[(trimethylsilyl)oxy]disiloxanyl]propyl]phenol | 155633-54-8 |
| 39 | 1,1-[(2,2'-Dimethylpropoxy)carbonyl]-4,4-diphenyl-1,3-butadiene | 363602-15-7 |

Polymeric or polymer-bonded filter substances can also be used according to the invention.

The cosmetic and dermatological preparations according to the invention can additionally advantageously comprise inorganic pigments based on metal oxides and/or other metal compounds which are insoluble or sparingly soluble in water, selected from the group consisting of the oxides of iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides.

For the purposes of the present invention, it is particularly advantageous, although not obligatory, for the inorganic pigments to be in coated form, i.e. to have been surface-treated. This surface treatment may involve for example providing the pigments with a thin hydrophobic layer by a method known per se, as described in DE-A-33 14 742.

To protect human hair from UV rays, the light protection agent formulations according to the invention can be incorporated into shampoos, lotions, gels, hairsprays, aerosol foam creams or emulsions in concentrations of from 0.1 to 10% by weight, preferably 1 to 7% by weight. The respective formulations can inter alia be used for washing, coloring and for styling hair.

The formulations to be used according to the invention are usually notable for a particularly high absorbance in the UV-A radiation region with a sharp band structure. Moreover, they are readily soluble in cosmetic oils and can easily be incorporated into cosmetic formulations. The emulsions prepared with the formulations are particularly notable for their high stability, the formulations I themselves are notable for their high photostability, and the preparations prepared therewith are notable for their pleasant feel on the skin.

The UV filter action of the formulations according to the invention can also be utilized for stabilizing active ingredients and auxiliaries in cosmetic and pharmaceutical formulations.

The preparations according to the invention are notable for particularly high absorbance in the UV-A radiation region with a sharp band structure and high light protection factors.

EXAMPLE 1

General Batch Process for Surface Treating Zinc Oxide and/or Titania Particles The method comprises introducing zinc oxide and/or titania particles comprising a plurality of nanoparticles into a surface treatment vessel that is capable of mixing and heating its contents under a controlled environment. Example of suitable surface treatment vessels comprise a Buchi Rotovap (small scale available from Brinkmann Instruments), V-blender (commercial scale available from Patterson-Kelley), ribbon-blender (commercial scale available from Jaygo), rotary oven (commercial scale available from Thermal Processing Solutions), and a fluidized bed (commercial scale available from Littleford Day).

a) The particles are introduced into the surface treatment vessel using methods known to those skilled in the art. Oxygen is removed from the vessel, typically by vacuum followed by inert gas flush, and the plurality of nanoparticles is mixed by methods such as, but not limited to, rotating the vessel or by rotating elements within the vessel. The particles are substantially spherical nanocrystalline nanoparticles and readily flow using standard unit operation methodologies. Particle mixing is carried out at a temperature, in an environment, and for a time that is effective at exposing particulate surface area to the environment of the surface treatment vessel enabling conditioning of the particle surface. Mixing may occur continuously, or at programmed intervals, and at a range of mixing rates. Mixing may occur at room temperature or at temperatures above or below room temperature depending on the chemistry of the surface treated particles. The degree of mixing may be used to control the bulk density of the final product—greater mixing yields a higher bulk density particulate product.

b) Particle surface conditioning comprises, but is not limited to, removing material sorbed to the particle surface, adding dopants to the particle surface, or a combination of conditioning steps. Particle surface conditioning may be accomplished by, but is not limited to, the following unit operations: vacuum treatment, plasma treatment, washing or flushing or fluidizing with a gas, fluid washing, reactive gas or fluid treatment, etc. In all instances reactive by-products and residues are removed prior to the application of surface treatment precursors.

c) Subsequent to particle surface conditioning, the particles are mixed with surface treatment precursors and heated in an environment, to a pre-determined temperature, and for a time effective for the star-graft copolymer to coat the nanocrystalline zinc oxide and/or titania particle and the difunctional precursors to polymerize to form the looped and/or linear chains on the star-graft copolymer. During surface treatment particulate mixing enables continuous surface exposure and promotes application of a uniform surface treatment to the plurality of particles. The nanoparticles and the coating precursor are added in relative quantities effective to enable a personal care application. The amount of coating precursor used is directly related to the particle surface area or the particle size.

d) Surface treatment sequences may include, but are not limited by, the followings process sequences: particle conditioning followed by surface treatment as in b) and c) above, multiple particle conditioning steps followed by surface treatment, particle conditioning followed by multiple surface treatment steps, sequential particle conditioning—surface treatment—particle conditioning—surface treatment steps, and others imagined by those skilled in the art.

e) The particles may comprise a single composition or multiple compositions.

f) Methods of introducing the surface treatment precursors may include, but are not limited by, fluid spray or vapor flow, employing any metered technique known to those skilled in the art.

g) The surface treatment precursors may be introduced as a precursor mixture, as a precursor mixture followed by a single precursor, or by sequential single precursor additions.

h) The surface treated particles are dried, if wet, cooled to room temperature, if reaction occurs at elevated temperature, and removed from the surface treatment vessel.

EXAMPLE 2

Batch Process for Surface Treating Zinc Oxide

The following process description is for preparing surface treated zinc oxide particles. The surface treated zinc oxide is an active physical sunscreen ingredient for cosmetic formulations.

The product is prepared by the batch process detailed in Example 1.

a) 8-kg of zinc oxide nanoparticles, with a surface area of 14-$m^2$/g, is weighed into a plastic bag and manually charged into a clean, 2-$ft^3$ V-blender. Oxygen is removed by evacuating the V-blender to full vacuum level followed by vacuum relief of the V-blender with nitrogen. The evacuation and relieve cycle is repeated twice.

b) With the V-blender filled with inert gas, the V-blender is rotated at 5 RPM, and the V-blender is constantly flushed with nitrogen to condition the particles by removing sorbed materials.

c) Diphenyldimethoxysilane (168 g) and octyltriethoxysilane (42 g) monomers are homogeneously mixed using a paddle mixer to form approximately a Si(0, 20, 80, and 0) surface treatment precursor mixture (210 g total weight).

d) Subsequent to particle surface conditioning, the surface treatment precursor mixture is introduced into the V-blender through a nozzle by inert pressure displacement and sprayed on the particles as the particles are mixing at room temperature. The temperature continues to ramp to 105 to 115° C. Particle mixing and vapor-phase transport enable surface treatment precursors to wet the particles and react to coat the nanocrystalline zinc oxide. The temperature is maintained at 105 to 115° C. for 1-hour.

e) The surface treated zinc oxide is dried by pulling a vacuum, while purging the vessel with inert gas, $N_2$, on the surface treatment vessel. Vacuum removes unreacted surface treatment precursors and reaction by-products. At the same time the temperature of the vessel is cooled to room temperature. The surface treated zinc oxide is removed from the vessel at room temperature.

The surface treatment on the zinc oxide product, when added to cosmetic formulation, prevents ion leakage and renders the surface treated zinc oxide compatible with charged organic moieties, such as acrylate-based polymers, α- and β-hydroxy acids. No other known commercial product or known surface treatment on zinc oxide particles enables the observed chemically passive behavior.

The above batch process may be scaled to surface treat larger amounts of particles or rendered continuous, as will be recognized by persons skilled in the art, by employing continuous mixing and heating equipment and appropriate process modifications.

EXAMPLE 3

Specific Surface Treatment Examples

1) Physical sunscreen ingredients—Si(20, 80)/octyltriethoxysilane, diphenyldimethoxysilane; 4.3 wt % surface treatment precursor mixture applied to ZnO (23 $m^2/g$).

2) Physical sunscreen ingredients—Si(20, 80)/octyltriethoxysilane, diphenyldimethoxysilane; approximately 9.4 wt % surface treatment precursor mixture applied to $TiO_2$ (50 $m^2/g$).

EXAMPLE 4

Cosmetic Formalations

Surface treated zinc oxide nanoparticles, produced by methods disclosed above, were incorporated into the oil in water formulations given in Tables 1–20 using the procedure following each respective table.

TABLE 1

| Formulation 1 | |
|---|---|
| Weight % | INCI - Names |
| Phase A | |
| 1.5 | Steareth-2 |
| 0.5 | Steareth-21 |
| 3.0 | Cetearyl Alcohol |
| 0.2 | Bees wax |
| 20.0 | Cetearyl Ethylhexanoate |
| 5.0 | Surface Treated Zinc Oxide |
| Phase B | |
| 0.3 | Acrylates/$C_{10}$–$C_{30}$ Alkyl Acrylate Crosspolymer |
| ad 100 | Deionized Water |
| 0.04 | Triethanolamine |

Procedure: Formulation 1
1. Heat Phase A ingredients to 80° C.
2. Stir Phase A at 11000 rpm using a homogenizer for 3 minutes
3. Mix Phase B ingredients and heat them to 80° C.
4. Add Phase B to Phase A to form Mixture 1
5. Stir Mixture 1 at 11000 rpm using a homogenizer for 30 sec–1 min
6. Cool Mixture 1 to room temperature under gentle planetary mixing
7. Stir Mixture 1 at 11000 rpm using a homogenizer for 30 sec–1 min

TABLE 2

| Formulation 2 | |
|---|---|
| Weight % | INCI - Names |
| Phase A | |
| 1.5 | Steareth-2 |
| 0.5 | Steareth-21 |
| 3.0 | Cetearyl Alcohol |
| 0.2 | Bees wax |

TABLE 2-continued

| Formulation 2 | |
|---|---|
| Weight % | INCI - Names |
| 20.0 | Cetearyl Ethylhexanoate |
| 5.0 | Surface Treated Zinc Oxide |
| Phase B | |
| 0.2 | Acrylates/C10–30 Alkyl Acrylate Crosspolymer |
| 45.77 | Deionized Water |
| 0.04 | Triethanolamine |
| Phase C | |
| 0.1 | Acrylates/Acrylamide Copolymer, Mineral Oil, Polysorbate 85, Triethanolamine |
| 22.88 | Deionized Water |

Procedure: Formulation 2
1. Heat Phase A ingredients to 80° C.
2. Stir Phase A at 15000 rpm using a homogenizer for 3 minutes
3. Mix Phase B ingredient and heat them to 80° C.
4. Mix Phase C ingredients and heat them to 80° C.
5. Mix Phase B and Phase C to form Mixture 1
6. Add Mixture 1 to Phase A to form Mixture 2.
7. Stir Mixture 2 at 11000 rpm using a homogenizer for 30 sec–1 min
8. Cool Mixture 2 to room temperature under gentle planetary mixing
9. Stir Mixture 1 at 11000 rpm using a homogenizer for 30 sec–1 min

TABLE 3

| Formulation 3 | |
|---|---|
| Weight % | INCI - Names |
| Phase A | |
| 8.0 | Dibutyl Adipate |
| 8.0 | $C_{12}$–$C_{15}$ Alkyl Benzoate |
| 12.0 | Cocoglycerides |
| 1.0 | Sodium Cetearyl Sulfate |
| 4.0 | Lauryl Glucoside and Polyglyceryl-2 Dipolyhydroxystearate and Glycerin |
| 2.0 | Ceteraryl Alcohol |
| 5.0 | Surface Treated Zinc Oxide |
| Phase B | |
| 3.0 | Glycerin |
| 0.05 | Disodium EDTA |
| 0.2 | Allantoin |
| 0.3 | Carbomer |
| ad 100 | Demineralized Water |
| 0.04 | Triethanolamine |
| Phase C | |
| 0.5 | DMDM Hydantoin |

Procedure: Formulation 3
1. Heat Phase A ingredients to 80° C.
2. Stir Phase A at 11000 rpm using a homogenizer for 3 minutes
3. Mix Phase B ingredients and heat them to 80° C.
4. Mix Phase B and Phase A to form Mixture 1
5. Stir Mixture 1 at 11000 rpm using a homogenizer for 30 sec–1 min
6. Cool Mixture 1 to room temperature under gentle planetary mixing.
7. Mix Phase C to Mixture 1 at 11000 rpm using a homogenizer for 30 sec–1 min

TABLE 4

| Formulation 4 | |
|---|---|
| % | INCI - Names |
| Phase A | |
| 7.50 | Ethylhexyl Methoxycinnamate |
| 1.50 | Polysorbate 20 |

TABLE 4-continued

Formulation 4

| % | INCI - Names |
|---|---|
| 3.00 | Sodium Lauryl Lactylate |
| 1.00 | PEG - 40 Hydrogenated Castor Oil |
| 1.00 | Butyrospermum Parkii (Shea Butter) |
| 6.50 | $C_{12}$–$C_{15}$ Alkyl Benzoate |
| | Phase B |
| 5.00 | Surface Treated Zinc Oxide |
| | Phase C |
| 4.00 | Glycerin |
| 1.00 | Panthenol, Propylene Glycol |
| 0.30 | Xanthan gum |
| 0.10 | Disodium EDTA |
| 2.00 | Urea |
| 2.00 | Hydroxyethyl Acrylate/Sodium Acryloyldimethyl Taurate Copolymer, Squalane, Polysorbate 60 |
| ad 100 | Demineralized Water |
| | Phase D |
| 0.50 | Lactic acid |
| 0.50 | Phenoxyethanol, Methylparaben, Butylparaben, Ethylparaben, Propylparaben, Isobutylparaben |

Procedure: Formulation 4
1. Heat Phase A ingredients to 80° C.
2. Add Phase B with Phase A and mix to form Mixture 1 using a homogenizer at 15000 rpm for 3 minutes
3. Mix Phase C ingredients and heat them to 80° C.
4. Mix Mixture 1 and Phase C to form Mixture 2 using a homogenizer at 11000 rpm for 3 minutes
5. Add Phase D ingredients to Mixture 2 to form Mixture 3 using a homogenizer at 11000 rpm 30 sec–1 min
6. Cool Mixture 3 to room temperature under gentle planetary mixing
7. Stir Mixture 1 at 11000 rpm using a homogenizer for 30 sec–1 min

TABLE 5

Formulation 5

| Weight % | INCI - Names |
|---|---|
| | Phase A |
| 1.00 | Ceteareth-25 |
| 2.00 | Ceteareth-6, Stearyl Alcohol |
| 2.00 | PEG-14 Dimethicone |
| 3.60 | Cetearyl Alcohol |
| 6.00 | Ethylhexyl Methoxycinnamate |
| 2.00 | Dibutyl Adipate |
| 5.00 | Surface Treated Zinc Oxide |
| | Phase B |
| 1.00 | Panthenol |
| 5.00 | Glycerin |
| ad 100 | Demineralized Water |
| | Phase C |
| 4.00 | Caprylic/Capric Triglyceride, Sodium Acrylates Copolymer |
| | Phase D |
| 0.50 | Phenoxyethanol, Methylparaben, Butylparaben, Ethylparaben, Propylparaben, Isobutylparaben |

Procedure: Formulation 5
1. Heat Phase A ingredients to 80° C.
2. Stir Phase A at 11000 rpm using a homogenizer for 3 minutes
3. Heat Phase B ingredients to 80° C.
4. Add Phase B with Phase A and mix to form Mixture 1 using a homogenizer at 11000 rpm for 30 sec–1minute.
5. Mix Phase C to Mixture 1 to form Mixture 2 using a homogenizer at 11000 rpm for 30 sec–1minute
6. Add Phase D ingredients to Mixture 2 while cooling to room temperature under gentle planetary mixing
7. Stir Mixture 1 at 11000 rpm using a homogenizer for 30 sec–1 min

TABLE 6

Formulation 6

| Weight % | INCI - Names |
|---|---|
| | Phase A |
| 3.0 | Steareth-21 |
| 2.0 | Cetearyl Alcohol |
| 6.0 | Ethylhexyl Methoxycinnamate |
| 2.0 | $C_{12}$–$C_{15}$-Alkyl Benzoate |
| 5.0 | Surface Treated Zinc Oxide |
| 3.0 | VP/Eicosene Copolymer |
| | Phase B |
| 5.0 | Glycerin |
| 2.0 | Hydroxyethyl Acrylates/Sodium Acryloyl |
| ad 100 | Deionized Water |
| 3.0 | Potassium Cetyl Phosphate |
| 0.1 | Disodium EDTA |
| | Phase C |
| 0.5 | Phenoxyethanol, Methylparaben, Ethylparaben, Butylparaben, Propylparaben |

Procedure: Formulation 6
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing

TABLE 7

Formulation 7

| Weight % | INCI - Names |
|---|---|
| | Phase A |
| 3.0 | Steareth-21 |
| 2.0 | Cetearyl Alcohol |
| 6.0 | Ethylhexyl Methoxycinnamate |
| 2.0 | $C_{12}$–$C_{15}$-Alkyl Benzoate |
| 5.0 | Surface Treated Zinc Oxide |
| 3.0 | VP/Eicosene Copolymer |
| | Phase B |
| 5.0 | Glycerin |
| 2.0 | Acrylates/$C_{10}$–$C_{30}$ Alkylacrylate Crosspolymer |
| ad 100 | Deionized Water |
| 0.04 | Triethanolamine |
| 3.0 | Potassium Cetyl Phosphate |
| 0.1 | Disodium EDTA |
| | Phase C |
| 0.5 | Phenoxyethanol, Methylparaben, Ethylparaben, Butylparaben, Propylparaben |

Procedure: Formulation 7
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing

TABLE 8

Formulation 8

| Weight % | INCI - Names |
|---|---|
| | Phase A |
| 3.0 | Steareth-21 |
| 2.0 | Cetearyl Alcohol |
| 6.0 | Ethylhexyl Methoxycinnamate |

TABLE 8-continued

Formulation 8

| Weight % | INCI - Names |
|---|---|
| 2.0 | Isohexadecane |
| 3.0 | Surface Treated Zinc Oxide |
| 3.0 | VP/Eicosene Copolymer |
| | Phase B |
| 5.0 | Glycerin |
| 0.3 | Acrylates/$C_{10}$–$C_{30}$ Alkylacrylate Crosspolymer |
| ad 100 | Deionized Water |
| 0.06 | Triethanolamine |
| 3.0 | Potassium Cetyl Phosphate |
| 0.1 | Disodium EDTA |
| | Phase C |
| 0.5 | Phenoxyethanol, Methylparaben, Ethylparaben, Butylparaben, Propylparaben |

Procedure: Formulation 8
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing

TABLE 9

Formulation 9

| Weight % | INCI - Names |
|---|---|
| | Phase A |
| 8.0 | Dibutyl Adipate |
| 8.0 | $C_{12}$–$C_{15}$-Alkyl Benzoate |
| 12.0 | Cocoglycerides |
| 1.0 | Sodium Cetearyl Sulfate |
| 4.0 | Lauryl Glucoside, Polyglyceryl-2 Dipolyhydroxystearate |
| 2.0 | Cetearyl Sulfate |
| 5.0 | Surface Treated Zinc Oxide |
| | Phase B |
| 3.0 | Glycerin |
| 0.05 | Disodium EDTA |
| 0.2 | Allantoin |
| 0.3 | Carbomer |
| ad 100 | Deionized Water |
| 0.04 | Triethanolamine |
| 3.0 | Potassium Cetyl Phosphate |
| | Phase C |
| 0.5 | DMDM Hydantoin |

Procedure: Formulation 9
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing

TABLE 10

Formulation 10

| Weight % | INCI - Names |
|---|---|
| | Phase A |
| 8.0 | Dibutyl Adipate |
| 8.0 | $C_{12}$–$C_{15}$-Alkyl Benzoate |
| 12.0 | Cocoglycerides |
| 1.0 | Sodium Cetearyl Sulfate |
| 4.0 | Lauryl Glucoside, Polyglyceryl-2 Dipolyhydroxystearate |
| 2.0 | Cetearyl Alcohol |

TABLE 10-continued

Formulation 10

| Weight % | INCI - Names |
|---|---|
| 5.0 | Surface Treated Zinc Oxide |
| 2.0 | Ethylhexyl Triazone |
| | Phase B |
| 3.0 | Glycerin |
| 0.05 | Disodium EDTA |
| 0.2 | Allantoin |
| 0.3 | Carbomer |
| ad 100 | Deionized Water |
| 0.04 | Triethanolamine |
| 3.0 | Potassium Cetyl Phosphate |
| | Phase C |
| 0.5 | DMDM Hydantoin |

Procedure: Formulation 10
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing

TABLE 11

Formulation 11

| Weight % | INCI - Names |
|---|---|
| | Phase A |
| 3.0 | Steareth-21 |
| 2.0 | Cetearyl Alcohol |
| 3.0 | Ethylhexyl Methoxycinnamate |
| 3.0 | Octocrylene |
| 2.0 | $C_{12}$–$C_{15}$-Alkyl Benzoate |
| 5.0 | Surface Treated Zinc Oxide |
| 3.0 | VP/Eicosene Copolymer |
| | Phase B |
| 5.0 | Glycerin |
| 2.0 | Acrylates/$C_{10}$–$C_{30}$ Alkylacrylate Crosspolymer |
| ad 100 | Deionized Water |
| 0.04 | Triethanolamine |
| 3.0 | Potassium Cetyl Phosphate |
| 0.1 | Disodium EDTA |
| | Phase C |
| 0.5 | Phenoxyethanol, Methylparaben, Ethylparaben, Butylparaben, Propylparaben |

Procedure: Formulation 11
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing

TABLE 12

Formulation 12

| Weight % | INCI - Names |
|---|---|
| | Phase A |
| 3.0 | Steareth-21 |
| 2.0 | Cetearyl Alcohol |
| 4.0 | Ethylhexyl Methoxycinnamate |
| 2.0 | 2-(4-Ethoxy-anilinomethylene)-propanedioic acid diethyl ester |
| 2.0 | $C_{12}$–$C_{15}$-Alkyl Benzoate |

TABLE 12-continued

Formulation 12

| Weight % | INCI - Names |
|---|---|
| 5.0 | Surface Treated Zinc Oxide |
| 3.0 | VP/Eicosene Copolymer |
| | Phase B |
| 5.0 | Glycerin |
| 2.0 | Acrylates/$C_{10}$–$C_{30}$ Alkylacrylate Crosspolymer |
| ad 100 | Deionized Water |
| 0.04 | Triethanolamine |
| 3.0 | Potassium Cetyl Phosphate |
| 0.1 | Disodium EDTA |
| | Phase C |
| 0.5 | Phenoxyethanol, Methylparaben, Ethylparaben, Butylparaben, Propylparaben |

Procedure: Formulation 12
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing

TABLE 13

Formulation 13

| Weight % | INCI - Names |
|---|---|
| | Phase A |
| 3.0 | Steareth-21 |
| 2.0 | Cetearyl Alcohol |
| 4.0 | Ethylhexyl Methoxycinnamate |
| 2.0 | Drometrizole Trisiloxane |
| 2.0 | $C_{12}$–$C_{15}$-Alkyl Benzoate |
| 5.0 | Surface Treated Zinc Oxide |
| 3.0 | VP/Eicosene Copolymer |
| | Phase B |
| 5.0 | Glycerin |
| 2.0 | Acrylates/$C_{10}$–$C_{30}$ Alkylacrylate Crosspolymer |
| ad 100 | Deionized Water |
| 0.04 | Triethanolamine |
| 3.0 | Potassium Cetyl Phosphate |
| 0.1 | Disodium EDTA |
| | Phase C |
| 0.5 | Phenoxyethanol, Methylparaben, Ethylparaben, Butylparaben, Propylparaben |

Procedure: Formulation 13
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing

TABLE 14

Formulation 14

| Weight % | INCI - Names |
|---|---|
| | Phase A |
| 3.0 | Ethylhexyl Methoxycinnamate |
| 1.0 | Diethylamino Hydroxybenzoyl Hexyl Benzoate |
| 3.0 | $C_{12}$–$C_{15}$-Alkyl Benzoate |
| 0.5 | Bees wax |
| 3.0 | Ceteareth-6, Stearyl Alcohol |
| 1.0 | Cetearyth-25 |
| 3.0 | Cetearyl Alcohol |

TABLE 14-continued

Formulation 14

| Weight % | INCI - Names |
|---|---|
| 5.0 | Caprylic/Capric Triglyceride |
| 3.0 | Surface Treated Zinc Oxide |
| 2.0 | Surface Treated Titanium Dioxide |
| | Phase B |
| 2.0 | Hydroxyethylacrylate/sodium acrylodimethyltaurate copolymer & Squalane & Polysorbate 60 |
| ad 100 | Deionized Water |
| | Phase C |
| 0.5 | Benzyl Alcohol, Methylchloroisothiazolinone, Methylisothiazolinone |

Procedure: Formulation 14
1. Heat Phase A and Phase B separately to about 80° C.
2. Homogenize Phase A and Phase B at 11000 rpm using a homogenizer for 3 minutes
3. Stir Phase B into Phase A and homogenize
4. Cool Mixture 3 to room temperature under gentle planetary mixing
5. Stir in Phase C and homogenize

TABLE 15

Formulation 15

| Weight % | INCI - Names |
|---|---|
| | Phase A |
| 3.0 | Ethylhexyl Methoxycinnamate |
| 1.0 | Diethylamino Hydroxybenzoyl Hexyl Benzoate |
| 3.0 | $C_{12}$–$C_{15}$-Alkyl Benzoate |
| 0.5 | Bees wax |
| 3.0 | Ceteareth-6, Stearyl Alcohol |
| 1.0 | Cetearyth-25 |
| 3.0 | Cetearyl Alcohol |
| 5.0 | Isohexadecane |
| 3.0 | Surface Treated Zinc Oxide |
| 2.0 | Surface Treated Titanium Dioxide |
| | Phase B |
| 0.3 | Carbomer |
| 0.04 | Triethanolamine |
| ad 100 | Deionized Water |
| | Phase C |
| 0.5 | Benzyl Alcohol, Methylchloroisothiazolinone, Methylisothiazolinone |

Procedure: Formulation 15
1. Heat Phase A and Phase B separately to about 80° C.
2. Homogenize Phase A and Phase B at 11000 rpm using a homogenizer for 3 minutes
3. Stir Phase B into Phase A and homogenize
4. Cool Mixture 3 to room temperature under gentle planetary mixing
Stir in Phase C and homogenize

TABLE 16

Formulation 16

| Weight % | INCI - Names |
|---|---|
| | Phase A |
| 4.0 | Glyceryl Stearate, PEG-100 Stearate |
| 3.0 | Ethylhexyl Methoxycinnamate |
| 1.0 | Diethylamino Hydroxybenzoyl Hexyl Benzoate |
| 0.5 | Lecithin |
| 0.5 | Polyglyceryl Dimer Soyate |

TABLE 16-continued

Formulation 16

| Weight % | INCI - Names |
|---|---|
| | Phase B |
| 0.25 | Iron Oxides Braun 70 E 172 |
| 2.25 | Trimethylolpropane Triisostearate |
| | Phase C |
| 5.5 | Cyclopentasiloxane, Cyclohexasiloxane |
| 4.0 | Ethylhexyl Palmitate |
| 1.5 | Simmondsia Chinensis (Jojoba) Seed Oil |
| 2.0 | Propylene Glycol Dicaprylate/Dicaprate |
| 1.5 | Sweet Almond (Prunus Amygdalus Dulcis) Oil |
| 5.0 | Surface Treated Titanium Dioxide |
| 0.5 | Tocopheryl Acetate |
| 1.0 | Butyrospermum Parkii (Shea Butter) |
| 0.5 | Polyglyceryl-2 Dipolyhydroxystearate |
| | Phase D |
| 5.0 | Propylene Glicol |
| 0.5 | Poloxamer 188 |
| 0.1 | Disodium EDTA |
| ad 100 | Deionized Water |
| | Phase E |
| 2.00 | Hydroxyethylacrylate/sodium acrylodimethyltaurate copolymer & Squalane & Polysorbate 60 |
| | Phase F |
| 1.0 | Phenonip, Phenoxyethanol, Methylparaben, Ethylparaben, Butylparaben, Propylparaben, Isobutylparaben |
| 0.2 | Bisabolol |

Procedure: Formulation 16
1. Heat Phase A, B, C and Phase D separately to about 70° C.
2. Homogenize Phase B over a roller mill
3. Mix Phase B into Phase A and homogenize
4. Homogenize Phase C and stir into Phase A and B and homogenize at 12000 rpm
5. Dissolve Phase D and stir into combined Phase A, B and C and homogenize
6. Stir in Phase E and homogenize smoothly
7. Cool down to 40° C. under stirring
8. Add Phase F and homogenize

TABLE 17

Formulation 17

| Weight % | INCI - Names |
|---|---|
| | Phase A |
| 1.5 | Steareth-2 |
| 0.5 | Steareth-21 |
| 3.0 | Cetearyl Alcohol |
| 0.2 | Bees wax |
| 20.0 | Cetearyl Ethylhexanoate |
| | Phase B |
| 0.3 | Acrylates/$C_{10}$–$C_{30}$ Alkyl Acrylate Crosspolymer |
| ad 100 | Deionized Water |
| 0.04 | Triethanolamine |
| | Phase C |
| 5.0 | Surface Treated Zinc Oxide |

Procedure: Formulation 17
1. Heat Phase A ingredients to 80° C.
2. Stir Phase A at 11000 rpm using a homogenizer for 3 minutes
3. Mix Phase B ingredients and heat them to 80° C.
4. Add Phase C to Phase B and homogenize
5. Add Phase B/C to Phase A and homogenize
6. Cool Mixture to room temperature under gentle planetary mixing

TABLE 18

Formulation 18

| Weight % | INCI - Names |
|---|---|
| | Phase A |
| 3.0 | Diethylamino Hydroxybenzoyl Hexyl Benzoate |
| 2.5 | Di-$C_{12}$–$C_{13}$ Alkyl Malate |
| 0.5 | Tocopherylacetate |
| 1.0 | Sodium Cetearyl Sulfate |
| 4.0 | Polyglyceryl-3 Methyl Glucose Distearate |
| 1.0 | VP/Eicosene Copolymer |
| 1.0 | Glycerin |
| 5.0 | Caprylic/Capric Triglyceride |
| 3.0 | Surface Treated Zinc Oxide |
| | Phase B |
| 2.0 | Hydroxyethylacrylate/sodium acrylodimethyltaurate copolymer & Squalane & Polysorbate 60 |
| ad 100 | Deionized Water |

Procedure: Formulation 18
1. Heat Phase A and Phase B ingredients separately to 80° C.
2. Stir in Phase B into Phase A and homogenize
3. Cool Mixture to room temperature under gentle planetary mixing

TABLE 19

Formulation 19

| Weight % | INCI - Names |
|---|---|
| | Phase A |
| 3.0 | Avobenzone |
| 2.5 | Di-$C_{12}$–$C_{13}$ Alkyl Malate |
| 0.5 | Tocopherylacetate |
| 1.0 | Sodium Cetearyl Sulfate |
| 4.0 | Polyglyceryl-3 Methyl Glucose Distearate |
| 1.0 | VP/Eicosene Copolymer |
| 1.0 | Glycerin |
| 5.0 | Caprylic/Capric Triglyceride |
| 3.0 | Surface Treated Zinc Oxide |
| | Phase B |
| 2.0 | Hydroxyethylacrylate/sodium acrylodimethyltaurate copolymer & Squalane & Polysorbate 60 |
| ad 100 | Deionized Water |

Procedure: Formulation 19
1. Heat Phase A and Phase B ingredients separately to 80° C.
2. Stir in Phase B into Phase A and homogenize
3. Cool Mixture to room temperature under gentle planetary mixing

TABLE 20

Formulation 20

| Weight % | INCI - Names |
|---|---|
| | Phase A |
| 8.0 | Dibutyl Adipate |
| 8.0 | $C_{12}$–$C_{15}$-Alkyl Benzoate |
| 12.0 | Cocoglycerides |
| 1.0 | Sodium Cetearyl Sulfate |
| 4.0 | Lauryl Glucoside, Polyglyceryl-2 Dipolyhydroxystearate |
| 2.0 | Cetearyl Alcohol |
| 5.0 | Surface Treated Zinc Oxide |
| 2.0 | 1,1-[(2,2'-Dimethylpropoxy)carbonyl]-4,4-diphenyl-1,3-butadiene |
| | Phase B |
| 3.0 | Glycerin |
| 0.05 | Disodium EDTA |
| 0.2 | Allantoin |

TABLE 20-continued

Formulation 20

| Weight % | INCI - Names |
|---|---|
| 0.3 | Carbomer |
| ad 100 | Deionized Water |
| 0.04 | Triethanolamine |
| 3.0 | Potassium Cetyl Phosphate |
| | Phase C |
| 0.5 | DMDM Hydantoin |

Procedure: Formulation 20
1. Heat Phase A and Phase B ingredients separately to 80° C.
2. Homogenize Phase A and Phase B separately
3. Add Phase B to Phase A and homogenize for 3 minutes
4. Add Phase C to Phase A/B and homogenize
5. Cool Mixture 4 to room temperature under gentle planetary mixing The above examples are O/W dispersions used as sun care formulations. However the disclosed invention is not limited by these examples, may be extended to other skin care formulations containing all acceptable cosmetic ingredients for all personal care formulations.

While particular elements, embodiment, and applications of the present invention have been shown and described, it will be understood, of course, that the invention is not limited thereto since modifications may be made by those skilled in the art, particularly in light of the forgoing teachings. It is therefore contemplated by the appended claims to cover such modifications as incorporate those features which come within the spirit an scope of the invention.

What is claimed is:

1. A method of protecting human skin or human hair from ultraviolet radiation comprising treating said skin or hair with an effective protecting concentration of a surface treated particle comprising a plurality of zinc oxide and/or titania particles and a star-graft copolymer with looped and/or linear polymeric structure on a star-graft copolymer encapsulating at least a portion of said particles, said surface treatment comprising: Si (x, y) where x and y are mole percent trifunctional and difunctional monomeric units, respectively and wherein x and y are about 1–40 and 60–99, respectively, wherein: x is selected from the group of trifunctional monomers that have cosmetically acceptable non-reactive ligands comprising of methyltrimethoxysilane, n-propyltrimethoxysilane, isobutyltrimethoxysilane, n-hexyltrimethoxysilane, n-octyltrimethoxysilane, n-octadecyltrimethoxysi-lane, phenyltrimethoxysilane, and the triethoxy-containing counterparts of these monomers; y is selected from the group of difunctional monomers that have cosmetically acceptable non-reactive ligands comprising of dicyclohexyldimethoxysilane, diethyldiethoxysilane, dimethyldichlorosilane, dimethyldiethoxysilane, dimethyldimethoxysilane, diphenyldiethoxysilane, diphenyldimethoxysilane, di-n-hexyldichlorosilane-, n-hexylmethyldichlorosilane, methyldodecyldiethoxysilane, n-octylmethyldimethoxysilane, and the diethoxy-containing counterparts of these monomers, where the product(s) per se, defined as surface treated ZnO and/or TiO$_2$, are used in personal care formulations.

2. The method according to claim 1, wherein said surface treatment comprising: Si (x, y) wherein x and y are about 10–30 and 70–90, respectively, wherein: x is selected from the group of n-octyltrimethoxysilane, n-octyltriethoxysilane, phenyltrimethoxysilane and phenyltriethoxysilane, and y is selected from the group of n-octyltrimethoxysilane, n-octyltriethoxysilane.

3. The method according to claims 1, wherein said effective protecting concentration ranges between 0. 1% and 25% by weight, based on the total weight of the personal care formulation.

4. The method according to claim 1, wherein said personal care formulation comprises surface treated zinc oxide and/or titanium dioxide particles alone or together with compounds which absorb in the UV region and are known for cosmetic and pharmaceutical preparations.

5. A sunscreen-containing personal care formulation for protecting human skin or human hair from ultraviolet radiation, which comprises, in a cosmetically and pharmaceutically suitable carrier, an effective protecting concentration of a surface treated particle comprising a plurality of zinc oxide and/or titania particles and a star-graft copolymer with looped and/or linear polymeric structure on a star-graft copolymer encapsulating at least a portion of said particles, said coating polymer comprising: Si (x,y) where x and y are the mole percent trifunctional and difunctional monomeric units, respectively, and wherein x is about 1–40 and y is about 60–99, respectively, wherein: x is selected from the group of trifunctional monomers that have cosmetically acceptable non-reactive ligands comprising of methyltrimethoxysilane, n-propyltrimethoxysilane, isobutyltrimethoxysilane, n-hexyltrimethoxysilane, n-octyltrimethoxysilane, n-octadecyltrimethoxysilane, phenyltrimethoxysilane, and the triethoxy-containing counterparts of these monomers; y is selected from the group of difunctional monomers that have cosmetically acceptable non-reactive ligands comprising of dicyclohexyldimethoxysilane, diethyldiethoxysilane, dimethyldichlorosilane, dimethyldiethoxysilane, dimethyldimethoxysilane, diphenyldiethoxysilane, diphenyldimethoxysilane, di-n-hexyldichlorosilane, n-hexylmethyldichlorosilane, methyldodecyldiethoxysilane, n-octylmethyldimethoxysilane, and the diethoxy-containing counterparts of these monomers.

6. The personal care formulation according to claim 5, wherein said surface treatment comprising: Si (x, y) wherein x and y are about 10–30 and 70–90, respectively, wherein: x is selected from the group of n-octyltrimethoxysilane, n-octyltriethoxysilane, phenyltrimethoxysilane and phenyltriethoxysilane, and y is selected from the group of n-octyltrimethoxysilane, n-octyltriethoxysilane.

7. A surface treated particle comprising a plurality of zinc oxide and/or titania particles and a star-graft copolymer with looped and/or linear polymeric structure on a star-graft copolymer encapsulating at least a portion of said particles, said surface treatment comprising: Si (x, y) where x and y are mole percent trifunctional and difunctional monomeric units, respectively and wherein x and y are about 1–40 and 60–99, respectively, wherein: x is selected from the group of trifunctional monomers that have cosmetically acceptable non-reactive ligands comprising of methyltrimethoxysilane, n-propyltrimethoxysilane, isobutyltrimethoxysilane, n-hexyltrimethoxysilane, n-octyltrimethoxysilane, n-octadecyltrimethoxysilane, phenyltrimethoxysilane, and the triethoxy-containing counterparts of these monomers; y is selected from the group of difunctional monomers that have cosmetically acceptable non-reactive ligands comprising of dicyclohexyldimethoxysilane, diethyldiethoxysilane, dimethyldichlorosilane, dimethyldiethoxysilane, dimethyldimethoxysilane, diphenyldiethoxysilane, diphenyldimethoxysilane, di-n-hexyldichlorosilane, n-hexylmethyldichlorosilane, methyldodecyldiethoxysilane, n-octylmethyldimethoxysilane, and the diethoxy-containing counterparts of these monomers.

8. The surface treated zinc oxide and/or titania particle according to claim 7, wherein said surface treatment comprising: Si (x, y) wherein x and y are about 10–30 and 70–90, respectively, wherein: x is selected from the group of n-octyltrimethoxysilane, n-octyltriethoxysilane, phenyltrimethoxysilane and phenyltriethoxysilane, and y is selected from the group of n-octyltrimethoxysilane, n-octyltriethoxysilane.

9. The surface treated zinc oxide and/or titania particle according to claim 7, wherein the particles are nanocrystalline particles.

10. The surface treated zinc oxide and/or titania particle according to claim 7, wherein the particles are nanoparticles with a mean particle size range from about 1 nm to about 900 nm.

11. The surface treated zinc oxide and/or titania particle according to claim 7, where in the particles are nanoparticles with a mean particle size range from about 2 nm to about 500 nm.

12. The surface treated zinc oxide and/or titania particle according to claim 7, wherein the particles are nanoparticles with a mean particle size range from about 5 nm to about 100 nm.

13. The surface treated zinc oxide and/or titania particle according to claim 7, where x and y are about 10–30 and 70–90, respectively.

* * * * *